(12) United States Patent
Takahashi

(10) Patent No.: US 7,546,781 B2
(45) Date of Patent: Jun. 16, 2009

(54) ULTRASONIC OPERATION APPARATUS AND ABNORMALITY JUDGMENT METHOD THEREOF

(75) Inventor: Hiroyuki Takahashi, Tokyo (JP)

(73) Assignee: Olympus Corporation (JP)

( * ) Notice: Subject to any disclaimer, the term of this patent is extended or adjusted under 35 U.S.C. 154(b) by 16 days.

(21) Appl. No.: 11/673,392

(22) Filed: Feb. 9, 2007

(65) Prior Publication Data

US 2007/0167881 A1   Jul. 19, 2007

Related U.S. Application Data

(63) Continuation of application No. PCT/JP2005/013599, filed on Jul. 25, 2005.

(30) Foreign Application Priority Data

Aug. 9, 2004   (JP) ............... 2004-232452

(51) Int. Cl.
*G01D 21/00* (2006.01)
*A61B 17/32* (2006.01)
*G01R 15/00* (2006.01)

(52) U.S. Cl. .............. 73/866.5; 606/169; 702/57

(58) Field of Classification Search ......... 73/579, 73/602, 866.5; 702/57–59, 65–66, 75–77; 606/167–171; 601/2–4
See application file for complete search history.

(56) References Cited

U.S. PATENT DOCUMENTS

| | | | |
|---|---|---|---|
| 5,897,569 A * | 4/1999 | Kellogg et al. | 606/169 |
| 6,056,735 A * | 5/2000 | Okada et al. | 606/1 |
| 6,537,291 B2 | 3/2003 | Friedman et al. | |
| 6,569,109 B2 * | 5/2003 | Sakurai et al. | 601/2 |
| 6,623,423 B2 * | 9/2003 | Ozaki et al. | 600/104 |

(Continued)

FOREIGN PATENT DOCUMENTS

EP   1 199 045 A1   4/2002

(Continued)

OTHER PUBLICATIONS

International Search Report PCT/JP2005/013599 dated Oct. 11, 2005.

*Primary Examiner*—Helen C. Kwok
(74) *Attorney, Agent, or Firm*—Ostrolenk, Faber, Gerb & Soffen, LLP

(57) ABSTRACT

An ultrasonic operation apparatus comprises a hand piece accommodating an ultrasonic transducer for generating ultrasonic vibrations, a probe which is connected to the hand piece and to which the ultrasonic vibrations are conveyed, a drive signal generating unit for generating a first drive signal that drives the ultrasonic transducer, and a second drive signal the output level of which is different from the first drive signal and for outputting the generated drive signals to the ultrasonic transducer, an output detecting unit for detecting the output current and the output voltage of the second drive signal to the ultrasonic transducer, and a controlling unit, which controls the operations of the drive signal generating unit based on a phase difference between the output voltage and the output current of the second drive signal, for judging the running state of the probe or the hand piece by determining whether or not a resonance frequency at which the phase difference between the output voltage and the output current becomes almost zero can be detected within a predetermined range.

22 Claims, 11 Drawing Sheets

U.S. PATENT DOCUMENTS

| | | | |
|---|---|---|---|
| 6,666,860 B1 * | 12/2003 | Takahashi | 606/34 |
| 7,252,648 B2 * | 8/2007 | Honda et al. | 604/22 |
| 2002/0049551 A1 | 4/2002 | Friedman et al. | |
| 2004/0102709 A1 | 5/2004 | Tanaka | |

FOREIGN PATENT DOCUMENTS

| | | |
|---|---|---|
| JP | 7-313937 | 12/1995 |
| JP | 2000-287989 | 10/2000 |
| JP | 2001-258089 | 9/2001 |
| JP | 2002-186901 | 7/2002 |
| JP | 2002-224134 | 8/2002 |
| JP | 2003-610 | 1/2003 |
| JP | 2004-732 | 1/2004 |

* cited by examiner

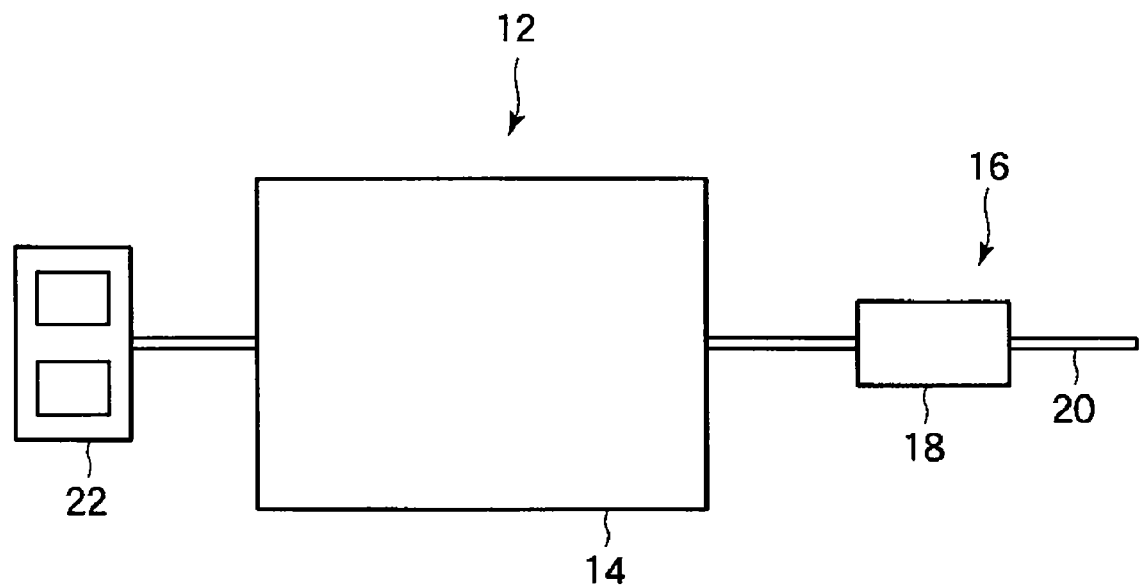
F I G. 1

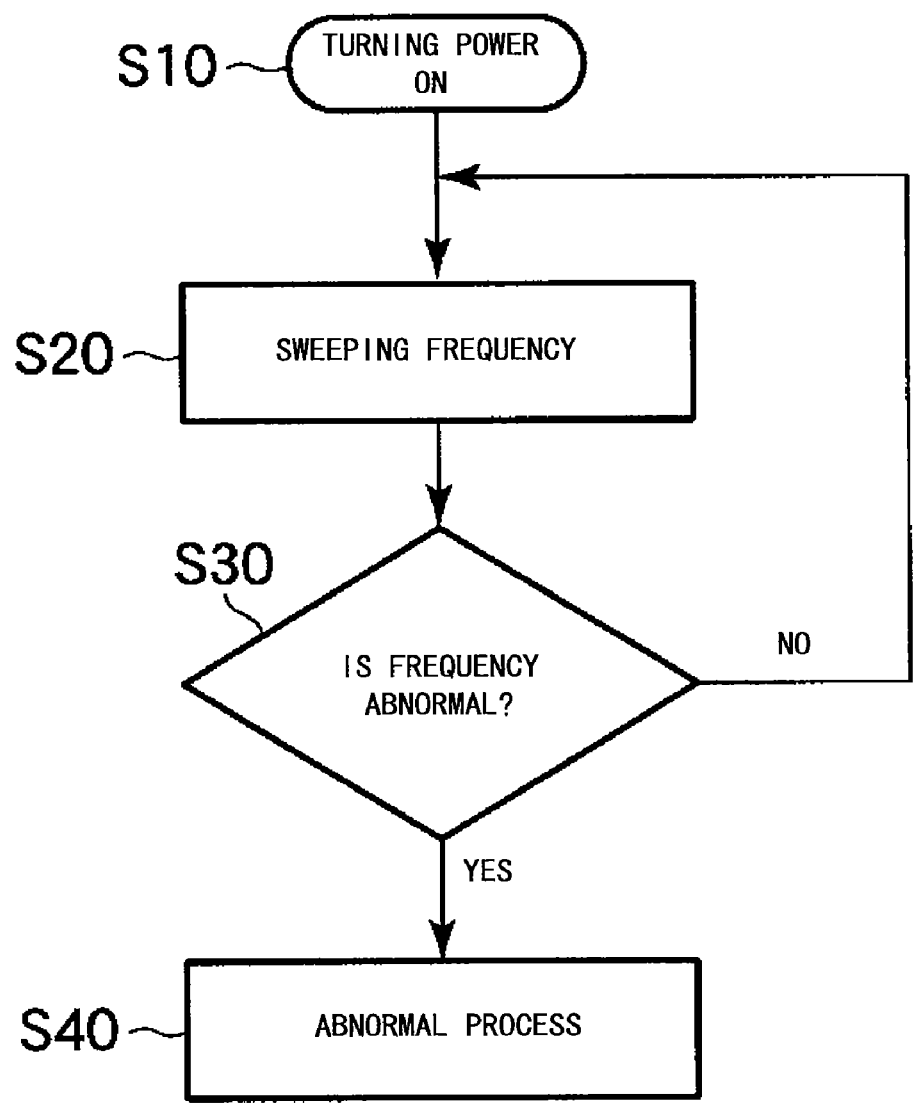
F I G. 3

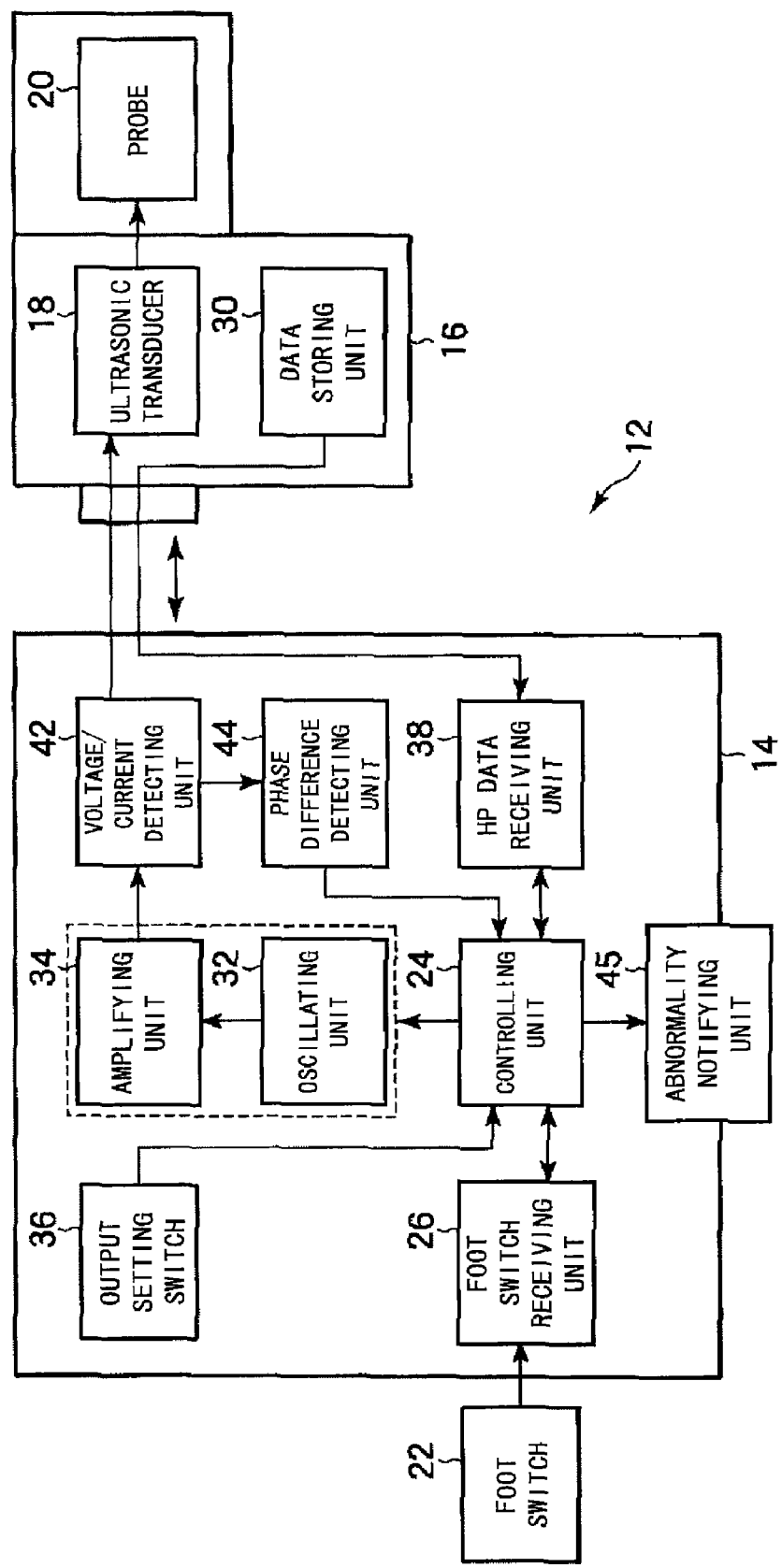
F I G. 4

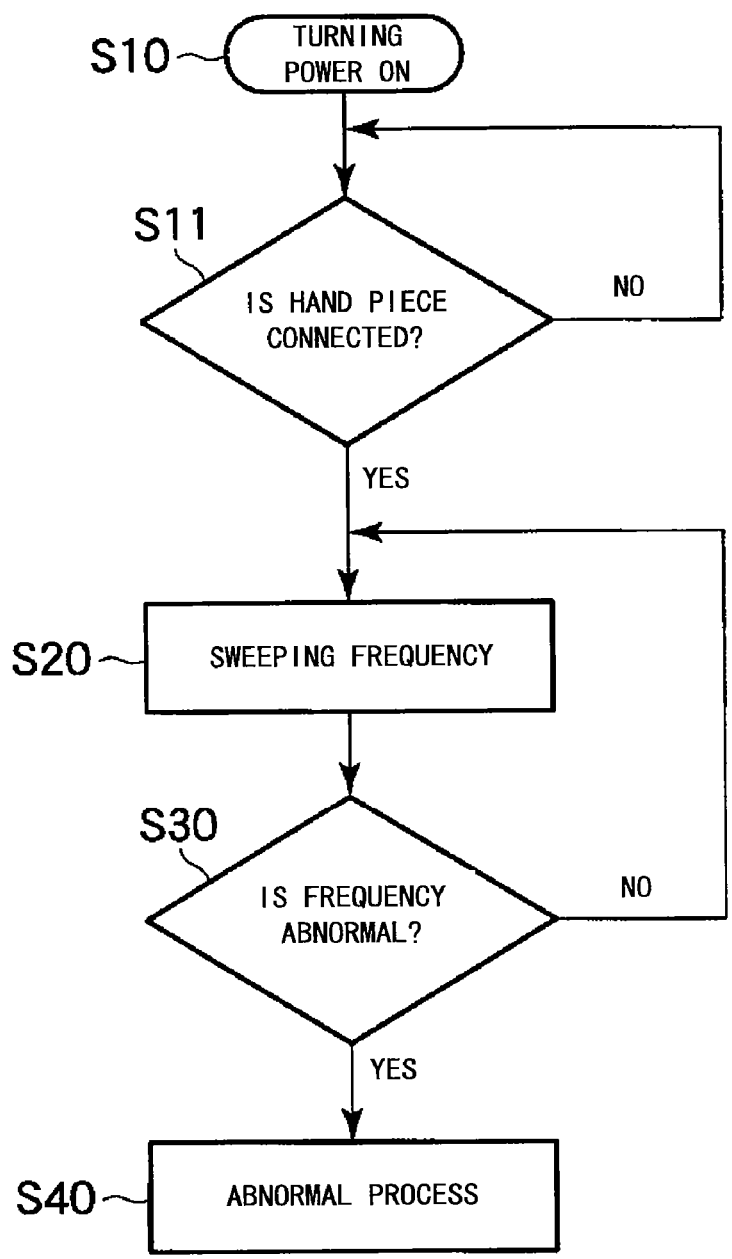
F I G. 5

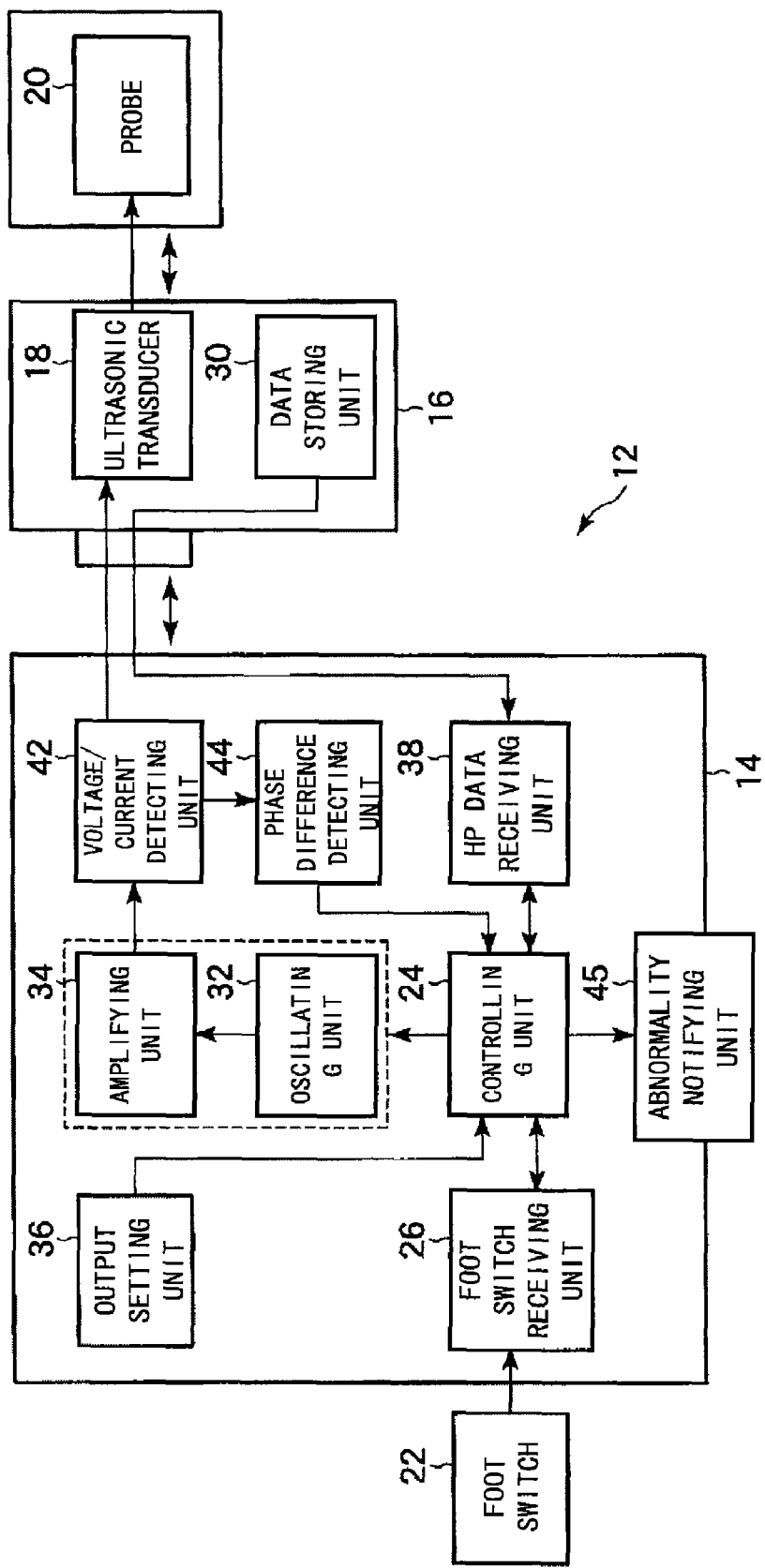
F I G. 6

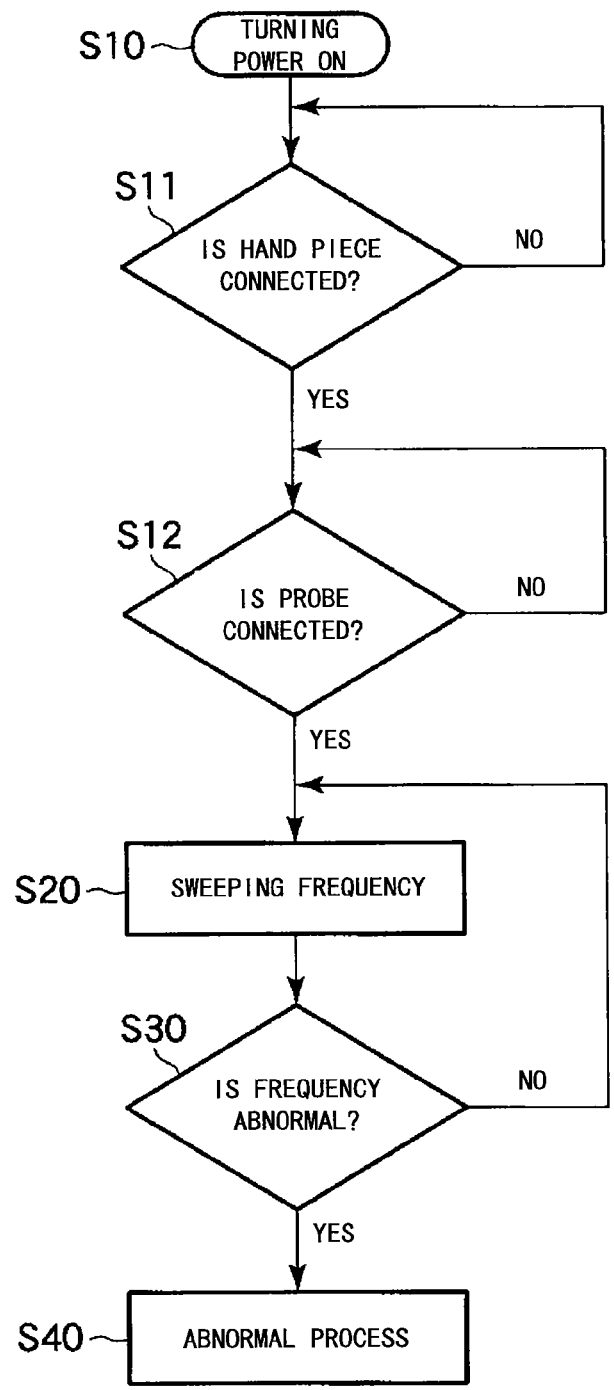
F I G. 7

ULTRASONIC OPERATION APPARATUS AND ABNORMALITY JUDGMENT METHOD THEREOF

CROSS REFERENCE TO RELATED APPLICATIONS

This is a Continuation Application of PCT Application No. PCT/JP2005/013599, filed Jul. 25, 2005, which was not published under PCT Article 21(2) in English.

This application is based upon and claims the benefit of priority from the prior Japanese Patent Application No. 2004-232452, filed Aug. 9, 2004, the entire contents of which are incorporated herein by reference.

BACKGROUND OF THE INVENTION

1. Field of the Invention

The present invention relates to an ultrasonic operation apparatus which can detect an abnormality, and an abnormality judgment method of the ultrasonic operation apparatus.

2. Description of the Related Art

Conventionally, an ultrasonic operation apparatus, such as an ultrasonic coagulation/incision apparatus or the like, for giving a treatment to a target to be treated with ultrasonic waves is used. Such an ultrasonic operation apparatus comprises an apparatus main body which generates a drive signal. To the apparatus main body, a hand piece (also called a hand instrument) is connected. This hand piece accommodates an ultrasonic transducer, to which the drive signal is input and which generates ultrasonic vibrations. To the hand piece, also the base of a probe which conveys the ultrasonic vibrations is connected. With the tip of the probe, a treatment is given to a target to be treated with the ultrasonic vibrations conveyed from the base of the probe to its tip.

Such an ultrasonic operation apparatus can increase the efficiency of a treatment by driving the hand piece at its resonance frequency. Here, a drive frequency at which a phase difference between an output voltage and an output current to the hand piece becomes 0 is the resonance frequency. In the ultrasonic operation apparatus, a PLL (Phase Locked Loop) control for controlling the drive signal is performed so that the phase difference between the output voltage and the output current becomes 0.

In the meantime, since a treatment is given by pressing the probe, which makes ultrasonic vibrations, against a target to be treated in the ultrasonic operation apparatus, a blade, etc. attached to the tip of the probe sometimes gets loose during the treatment, or a mechanical degradation can occur in the probe or the hand piece by continually applying a mechanical stress which occurs with the ultrasonic vibrations.

One example of the ultrasonic operation apparatus which can detect such abnormalities is disclosed by Patent Document 1. The ultrasonic operation apparatus of Patent Document 1 detects abnormalities such as a break, a crack, a blemish and the like of a probe. Namely, when an abnormality occurs in the probe, an abnormality is judged to occur in the probe when a resonance frequency changes from its normal value, namely, when the resonance frequency calculated under a PLL control goes out of a predetermined range. If the abnormality is judged to occur, an output to the hand piece is suspended, and the abnormality is notified with sound, light, vibrations or the like.

Similarly, an ultrasonic operation apparatus of Patent Document 2 records a resonance frequency in an early stage, and judges that an abnormality occurs in a probe or a hand piece if the resonance frequency changes from that in the early stage by a predetermined value or more.

Furthermore, an ultrasonic operation apparatus of Patent Document 3 obtains a frequency deviation, which is a difference between a prerecorded setting frequency and a calculated resonance frequency, and judges that an abnormality occurs in a probe or a hand piece if the frequency deviation goes out of a predetermined monitoring frequency range.

Still further, an ultrasonic converter of Patent Document 4 judges that an abnormality occurs in a probe or a hand piece if a calculated resonance frequency goes out of a predetermined resonance point tracking range.

Patent Documents 5 and 6 disclose ultrasonic operation systems which judge an abnormality separately from a PLL control. The ultrasonic operation system of Patent Document 5 detects the looseness of a blade attached to the tip of a probe. Namely, this ultrasonic operation system can calculate impedance from an output voltage and an output current, and recognizes a drive frequency, which minimizes the impedance, by sweeping the drive frequency of a drive signal to be a resonance frequency. The drive frequency is swept three times, and the resonance frequency is obtained each time the sweeping is made. If a change amount among the resonance frequencies is a stipulated value or larger, the blade is judged to be loose.

Additionally, the ultrasonic operation system of Patent Document 6 detects a crack of a probe. Namely, this ultrasonic operation system can obtain a resonance frequency from impedance similar to the ultrasonic operation system of Patent Document 5. This system sweeps a drive frequency twice with different excitation currents, obtains a resonance frequency each time the sweeping is made, and judges that a crack occurs in the probe if the resonance frequency in a low excitation current is lower than that in a high excitation current.

The ultrasonic operation apparatuses of Patent Documents 1 to 4 judge an abnormality in a PLL control. Namely, the apparatuses can detect an abnormality only when a drive signal is output to a hand piece, and cannot detect an abnormality except when an output is made. The ultrasonic operation systems of Patent Documents 5 and 6 can also detect an abnormality except when an output is made, but they must perform an impedance calculation, a comparison arithmetic, etc., leading to the complexity of the systems.

Patent Document 1: Japanese Published Unexamined Patent Application No. 2000-287989
Patent Document 2: Japanese Published Unexamined Patent Application No. 2001-258089
Patent Document 3: Japanese Published Unexamined Patent Application No. 2002-186901
Patent Document 4: Japanese Published Unexamined Patent Application No. H7-313937
Patent Document 5: Japanese Published Unexamined Patent Application No. 2002-224134
Patent document 6: Japanese Published Unexamined Patent Application No. 2003-610

SUMMARY OF THE INVENTION

The ultrasonic operation apparatus according to the present invention comprises: a hand piece accommodating an ultrasonic transducer that generates ultrasonic vibrations; a probe which is connected to the hand piece and to which the ultrasonic vibrations are conveyed; a drive signal generating unit for generating a first drive signal that drives the ultrasonic transducer, and a second drive signal the output level of which is different from the first drive signal, and for outputting the first and the second drive signals to the ultrasonic transducer; an output detecting unit for detecting an output current and an output voltage of the second drive signal to the ultrasonic transducer; and a controlling unit, which controls the operations of the drive signal generating unit based on a phase difference between the output voltage and the output current of the second drive signal, for judging the running state of the probe or the hand piece by determining whether or not a resonance frequency at which the phase difference between the output voltage and the output current becomes almost zero can be detected within a predetermined range.

Additionally, an abnormality judgment method of the ultrasonic operation apparatus, which comprises the hand piece accommodating the ultrasonic transducer that generates ultrasonic vibrations, and the probe which is connected to the hand piece and to which the ultrasonic vibrations are conveyed, according to the present invention comprises: generating a first drive signal that drives the ultrasonic transducer, and a second drive signal the output level of which is different from the first drive signal, and outputting the first and the second drive signals to the ultrasonic transducer; detecting the output current and the output voltage of the second drive signal to the ultrasonic transducer; and judging the running state of the probe or the hand piece by determining whether or not a resonance frequency at which a phase difference between the output voltage and the output current becomes almost zero can be detected within a predetermined range.

BRIEF DESCRIPTION OF THE DRAWINGS

FIG. 1 is a schematic showing a simplified configuration of the whole of an ultrasonic operation apparatus according to a first preferred embodiment of the present invention;

FIG. 3 is a flowchart for explaining a control performed by the ultrasonic operation apparatus according to the first preferred embodiment of the present invention;

FIG. 4 is a block diagram showing an ultrasonic operation apparatus according to a second preferred embodiment of the present invention;

FIG. 5 is a flowchart for explaining a control performed by the ultrasonic operation apparatus according to the second preferred embodiment of the present invention;

FIG. 6 is a block diagram showing an ultrasonic operation apparatus according to a third preferred embodiment of the present invention;

FIG. 7 is a flowchart for explaining a control performed by the ultrasonic operation apparatus according to the third preferred embodiment of the present invention;

DESCRIPTION OF THE PREFERRED EMBODIMENTS

Figure 2:
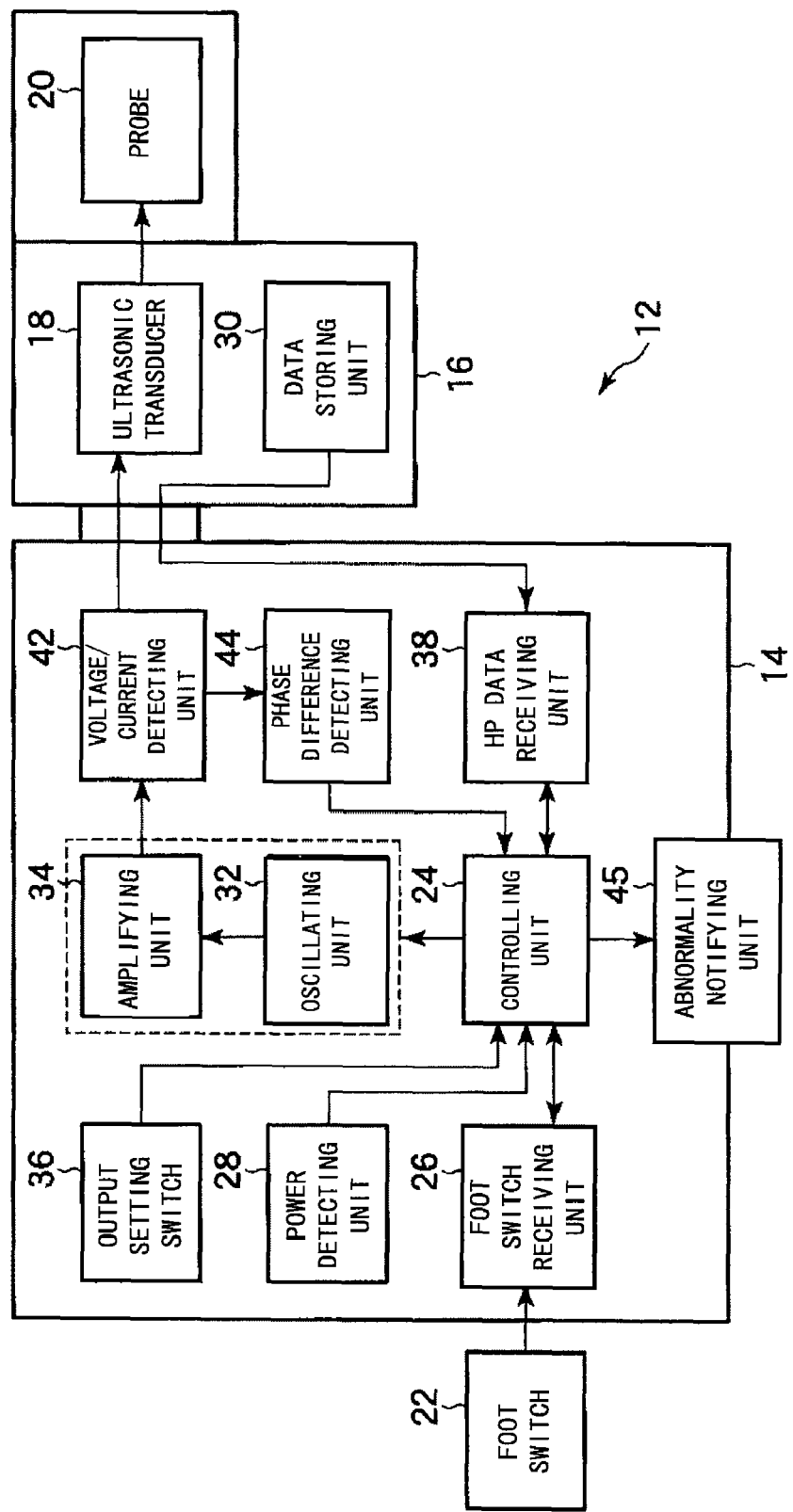
FIG. 2 is a block diagram showing the ultrasonic operation apparatus according to the first preferred embodiment of the present invention.

An object of the present invention is to provide an ultrasonic operation apparatus, which can also detect abnormalities of the ultrasonic operation apparatus even when an output is not made and the configuration of which is simple, and an abnormality judgment method of the ultrasonic operation apparatus. Preferred embodiments according to the present invention are hereinafter described.

First Preferred Embodiment

This preferred embodiment refers to an ultrasonic operation apparatus which can detect an abnormality of a hand piece or a probe from when the ultrasonic operation apparatus is powered on. The first preferred embodiment according to the present invention is described below with reference to FIGS. 1 to 3.

FIG. 1 is a schematic showing a simplified configuration of the whole of an ultrasonic operation apparatus 12 according to this preferred embodiment. This ultrasonic operation apparatus 12 comprises an apparatus main body 14 which generates a drive signal. To the apparatus main body 14, a hand piece 16 is connected.

The hand piece 16 accommodates an ultrasonic transducer 18. Additionally, the drive signal generated by the apparatus main body 14 is output to the ultrasonic transducer 18 within the hand piece 16. Furthermore, the ultrasonic transducer 18 within the hand piece 16 converts the input drive signal into mechanical vibrations to make ultrasonic vibrations.

Furthermore, to the hand piece 16, the base of a probe 20 which conveys the ultrasonic vibrations is connected. To the probe 20, the ultrasonic vibrations, which are generated by the ultrasonic transducer 18 within the hand piece 16, are conveyed. With the tip of the probe 20, a treatment is given to a target to be treated by using the ultrasonic vibrations conveyed from the base of the probe 20 to its tip. Besides, to the apparatus main body 14, a foot switch 22 for manipulating the apparatus main body 14 is connected.

FIG. 2 is a block diagram showing the ultrasonic operation apparatus according to the first preferred embodiment of the present invention. The apparatus main body 14 comprises a controlling unit 24 for controlling the apparatus main body 14. To the controlling unit 24, a foot switch receiving unit 26 is connected. The foot switch receiving unit 26 puts an ON/OFF signal input from the foot switch 22 into a digital code, and outputs the digital code to the controlling unit 24.

Additionally, to the controlling unit 24, a power detecting unit 28 as power detecting means for detecting ON/OFF of the power of the apparatus main body 14 is connected. This power detecting unit 28 detects the ON/OFF of the power, and outputs an ON/OFF signal, which is put into a digital code, to the controlling unit 24. Here, the ON/OFF signal of the foot switch receiving unit 26 is referred to as a first ON/OFF signal, whereas the ON/OFF signal of the power detecting unit 28 is referred to as a second ON/OFF signal.

In the meantime, a data storing unit 30, in which data of the hand piece 16 (hereinafter referred to as HP data) is recorded, is provided inside the hand piece 16. Examples of the HP data include the resonance frequency of the hand piece 16, the current value of the drive signal to the hand piece 16, the capacitance value of the hand piece 16 and the like. In this preferred embodiment, the drive current value of the second drive signal, a normal frequency range (or an abnormal frequency range), which is a reference for judging an abnormality of the hand piece 16, and a sweep frequency range for sweeping the drive frequencies of the first and the second drive signals are stored as the HP data in the data storing unit 30 as will be described later.

Here, as a storage medium of the data storing unit 30, a serial ROM, a parallel ROM or the like is used. If wires are desired to be reduced, a serial ROM is preferable. When the hand piece 16 is connected to the apparatus main body 14, the HP data is transmitted from the data storing unit 30 to the HP data receiving unit 38. The HP data receiving unit 38 puts the received HP data into a digital code, and outputs the digital code to the controlling unit 24.

Here, the control performed by the controlling unit 24 is summarized. Initially, upon receipt of the ON/OFF signal (the first or the second ON/OFF signal), the controlling unit 24 outputs a control signal (the first or the second control signal) to an oscillating unit 32. The oscillating unit 32 generates a drive signal (the first or the second drive signal) of a predetermined drive frequency based on the control signal, and outputs the generated drive signal to an amplifying unit 34. The drive signal from the amplifying unit 34 is output to the ultrasonic transducer 18 within the hand piece 16 via a voltage/current detecting unit 42. The voltage/current detecting unit 42 outputs detected current and voltage to a phase difference detecting unit 44. The phase difference detecting unit 44 detects a phase difference $\Delta\theta$ between the output voltage and the output current, and outputs the detected phase difference to the controlling unit 24. The controlling unit 24 outputs to the oscillating unit 32 a control signal for increasing/decreasing the drive frequency oscillated from the oscillating unit 32 based on the detected phase difference information. The oscillating unit 32 generates a drive signal based on the control signal, and outputs the generated drive signal to the amplifying unit 34. Such a control is repeated.

The controlling unit 24 outputs the first control signal to the oscillating unit 32 and the amplifying unit 34 if the first ON/OFF signal is ON. The oscillating unit 32 and the amplifying unit 34, to which the first control signal is input, output the first drive signal for driving the hand piece 16 to the hand piece 16. Namely, the oscillating unit 32 generates the first drive signal of a predetermined drive frequency, and outputs the generated first drive signal to the amplifying unit 34. The amplifying unit 34 amplifies the first drive signal to a predetermined drive current value, and outputs the first drive signal to the hand piece 16.

Here, the drive current value of the first drive signal is set as follows. In the apparatus main body 14, an output setting switch 36 for setting the output level of the hand piece 16 is provided. The output setting switch 36 outputs a setting signal according to an external input to the controlling unit 24. The controlling unit 24 sets a drive current value which realizes the size of a set output based on the setting signal.

Similarly, if the second ON/OFF signal is ON, the controlling unit 24 makes the oscillating unit 32 and the amplifying unit 34 output to the hand piece 16 the second drive signal of a predetermined drive frequency and a predetermined drive current value. The second drive signal is a signal intended to judge an abnormality of the hand piece 16. Additionally, the second drive signal is a drive signal, the output of which is smaller than the first drive signal, for feebly running the ultrasonic transducer 18.

The drive current value of the second drive signal is recorded in the data storing unit 30 as HP data. The controlling unit 24 sets the drive current value of the second drive signal based on the HP data input from the HP data receiving unit 38. As described above, the oscillating unit 32 and the amplifying unit 34 form the drive signal generating means for outputting the first and the second drive signals to the hand piece 16.

Between the amplifying unit 34 and the hand piece 16, the voltage/current detecting unit 42 as output detecting means for detecting the output voltages and the output currents of the first and the second drive signals, which are output to the hand piece 16, is provided. The voltage/current detecting unit 42 outputs detected current and voltage to a phase difference detecting unit 44. The phase difference detecting unit 44 detects a phase difference $\Delta\theta$ between the output voltage and the output current, and outputs the detected phase difference to the controlling unit 24.

Here, the resonance frequency of the hand piece 16 is almost determined in accordance with the standard of the hand piece 16, and exists within a predetermined frequency range (hereinafter referred to as a normal frequency range) even if an error of each hand piece 16 is considered. When an abnormality occurs in the hand piece 16 or the probe 20, the resonance frequency changes from its normal value. Therefore, if the resonance frequency of the second drive signal is not within the normal frequency range, it can be judged that the hand piece 16 or the probe 20 is abnormal.

As abnormalities of the hand piece 16 or the probe 20, a bad connection between the apparatus main body 14 and the hand piece 16 or between the hand piece 16 and the probe 20, a disconnection of a cable of the hand piece 16, defectiveness of a connector and the like are assumed in addition to mechanical damage of the hand piece 16 or the probe 20.

The controlling unit 24 judges such abnormalities, and has a function as an abnormal judging unit. Namely, a drive frequency at which the phase difference $\Delta\theta$ of the second drive signal, which is detected by the phase difference detecting unit 44, becomes 0 is the resonance frequency of the hand piece 16. The controlling unit 24 controls the drive frequency of the second drive signal so that $\Delta\theta$ becomes 0, detects the drive frequency at which $\Delta\theta$ becomes 0 as the resonance frequency, and judges whether or not the resonance frequency is within the normal frequency range. Note that the normal frequency range is recorded in the data storing unit 30 of the hand piece 16, transmitted from the data storing unit 30 to the HP data receiving unit 38, and input from the HP data receiving unit 38 to the controlling unit 24. Then, the controlling unit 24 judges that the hand piece 16 or the probe 20 is abnormal if the resonance frequency is not within the normal range, stops the second drive signal, and outputs a notification signal to abnormality notifying unit 45. The abnormality notifying unit 45 is a lamp, a buzzer or the like, which notifies an abnormality with sound, light or the like.

In the meantime, it is preferable to drive the hand piece 16 at its resonance frequency in order for an increase in a treatment efficiency. As described above, the drive frequency at which $\Delta\theta$ becomes 0 is a resonance frequency, and the controlling unit 24 controls the drive frequency of the first drive signal so that $\Delta\theta$ becomes 0. Such a control is called a PLL control. The PLL control can be realized with any of analog and digital circuits. However, since the analog circuit causes its specific fluctuations, temperature change and the like, it is preferable to use the digital circuit. The digital circuit is used in this preferred embodiment.

Note that the abnormality judgment of the hand piece 16 or the probe 20 is made also for the first drive signal in this preferred embodiment. Namely, even when the PLL control is performed for the first drive signal, which is output to the hand piece 16, the drive frequency at which $\Delta\theta$ becomes 0 is detected as a resonance frequency, and whether or not the resonance frequency is within a normal frequency range is judged. If the resonance frequency is not within the normal range, the controlling unit 24 judges that the hand piece 16 or the probe 20 is abnormal, stops the first drive signal, and outputs a notification signal to the abnormality notifying unit 45.

FIG. 3 is a flowchart for explaining the control performed by the ultrasonic operation apparatus according to the first preferred embodiment of the present invention. This figure depicts a flow for detecting an abnormality of the hand piece or the probe after power-on. When the ultrasonic operation apparatus 12 is used, the apparatus main body 14 is initially powered on in step S10. As a result, the power detecting unit 28 detects that the power is ON, and outputs the second ON/OFF signal to the controlling unit 24.

The controlling unit 24, to which the second ON/OFF signal is input, outputs the second control signal to the oscillating unit 32 and the amplifying unit 34, which then output the second drive signal to the hand piece 16, and whether or not the hand piece 16 or the probe 20 is abnormal is judged.

Namely, the controlling unit 24 reads a sweep frequency range transmitted from the data storing unit 30 of the hand piece 16 to the HP data receiving unit 38. Then, in step S20, the controlling unit 24 controls the oscillating unit 32 so that the drive frequency is swept from the upper limit to the lower limit (or from the lower limit to the upper limit) of the sweep frequency range. If the drive frequency output from the oscillating unit 32 is swept and the output current detected by the voltage/current detecting unit 42 becomes a stipulated value or larger, the controlling unit 24 judges that the drive frequency is in the neighborhood of the resonance frequency. Thereafter, the controlling unit 24 controls the drive frequency so that the phase difference $\Delta\theta$ between the output voltage and the output current becomes almost 0. If the controlling unit 24 judges that $\Delta\theta$ becomes almost 0, it detects the drive frequency as a resonance frequency. In the meantime, the controlling unit 24 reads the normal frequency range transmitted from the data storing unit 30 to the HP data receiving unit 38. Then, the controlling unit 24 judges whether or not the resonance frequency is within the normal frequency range.

If the output current does not become the stipulated value or larger as a result of sweeping the frequency, or if the resonance frequency is not within the normal frequency range when the output current becomes the stipulated value or larger, the controlling unit 24 judges in step S30 that the hand piece 16 or the probe 20 is abnormal. If the controlling unit 24 judges in step S30 that the hand piece 16 or the probe 20 is abnormal, the flow proceeds to step S40.

In step S40, the controlling unit 24 stops the second drive signal, outputs a notification signal to the abnormality notifying unit 45, which then notifies the abnormality with sound, light or the like.

Or, if the controlling unit 24 judges in step S30 that the hand piece 16 or the probe 20 is normal, the flow returns to step S20. Thereafter, the controlling unit 24 makes the abnormality judgment of the hand piece 16 or the probe 20 at predetermined time intervals.

When an output by the hand piece 16 is made, the output level of the hand piece 16 is set with an output setting switch 36. When the foot switch 22 is turned on, the controlling unit 24 stops the second control signal. Then, the controlling unit 24 outputs the first control signal to the oscillating unit 32 and the amplifying unit 34 based on the first ON/OFF signal from the foot switch 22 and the setting signal from the output setting switch 36. The oscillating unit 32 and the amplifying unit 34 output the first drive signal to the hand piece 16. At this time, the controlling unit 24 controls the first drive signal so that the hand piece 16 is driven at the resonance frequency.

This control is almost similar to that of the drive frequency of the second drive signal. Namely, the controlling unit 24 sweeps the drive frequency, and performs the PLL control for the drive frequency so that the phase difference $\Delta\theta$ between the output voltage and the output current becomes almost 0 if the output current becomes a stipulated value or larger. Note that the PLL control may be started in the neighborhood of the resonance frequency detected at the time of abnormality judgment without sweeping the frequency. Here, the resonance frequency is detected also in the PLL control. If the detected resonance frequency is not within the normal frequency range, the first drive signal is stopped, and an abnormality is notified similar to the time of the abnormality judgment.

Accordingly, the ultrasonic operation apparatus 12 according to this preferred embodiment produces the following effect. In this preferred embodiment, the first drive signal for giving a treatment to a target to be treated, and the second drive signal for judging an abnormality of the hand piece 16 or the probe 20 can be output to the hand piece 16. Accordingly, an abnormality of the hand piece 16 or the probe 20 can be judged by using the second drive signal unless the output of the hand piece 16 is made. Additionally, in the abnormality judgment, the drive frequency of the second drive signal is changed, attempts are made to detect a resonance frequency at which the phase difference between the output voltage and the output current to the hand piece 16 becomes almost zero, and it is judged that the hand piece 16 or the probe 20 is abnormal if the resonance frequency cannot be detected within a predetermined range. As described above, the abnormality judgment of the hand piece 16 or the probe 20 is easy, which simplifies the configuration of the apparatus main body 14 that makes the abnormality judgment.

In this preferred embodiment, the HP data is recorded in the data storing unit 30 of the hand piece 16, and read by the apparatus main body 14. Alternatively, a resistor element or the like for identifying the type of the hand piece 16 may be provided in the hand piece 16. In this case, HP data for each type of the hand piece 16 is recorded in the apparatus main body 14, the type of the hand piece 16 connected to the apparatus main body 14 is identified by the apparatus main body 14, and HP data corresponding to the type of the hand piece 16 is selected and used from among the recorded HP data.

Second Preferred Embodiment

The second preferred embodiment refers to an ultrasonic operation apparatus which detects an abnormality of a hand piece or a probe when the hand piece is connected to the ultrasonic operation apparatus after power-on. The second preferred embodiment of the present invention is described below.

FIG. 4 is a block diagram showing the ultrasonic operation apparatus according to the second preferred embodiment of the present invention. Constituent elements having functions similar to those in the first preferred embodiment are denoted with the same reference numerals, and their explanations are omitted. With reference to FIG. 4, the ultrasonic operation apparatus 12 according to this preferred embodiment makes abnormality judgment when the hand piece 16 is connected to an apparatus main body 14. In this preferred embodiment, the hand piece 16 is connectable/disconnectable to/from the apparatus main body 14. Additionally, a power detecting unit 28 (see FIG. 2) is not used in the apparatus main body 14. A controlling unit 24 has a function as hand piece connection detecting means for detecting whether or not the hand piece 16 is connected. Namely, the controlling unit 24 detects whether or not the hand piece 16 is connected based on whether or not HP data in the data storing unit 30 as storing means can be read.

FIG. 5 is a flowchart for explaining a control performed by the ultrasonic operation apparatus according to the second preferred embodiment of the present invention. This figure depicts a flow for detecting an abnormality of the hand piece or the probe after the connection of the hand piece is verified subsequently to power-on.

Firstly, in step S10, the apparatus main body 14 is powered on. Then, in step S11, the controlling unit 24 attempts to read HP data. If the controlling unit 24 can read the HP data, it judges that the hand piece 16 is connected. If the controlling unit 24 cannot read the HP data, it judges that the hand piece 16 is not connected.

If the controlling unit 24 judges in step S11 that the hand piece 24 is not connected, step S11 is repeated. Or, if the controlling unit 24 judges in step S11 that the hand piece 16 is connected, the flow proceeds to step S20. Thereafter, the abnormality judgment is repeated in a similar manner as in the first preferred embodiment.

Accordingly, the ultrasonic operation apparatus 12 according to this preferred embodiment produces the following effect. If the abnormality judgment is made in a state where the hand piece 16 is not connected to the apparatus main body 14, the controlling unit 24 judges that the hand piece 16 or the probe 20 is abnormal. In this preferred embodiment, the abnormality judgment of the hand piece 16 or the probe 20 is made when the hand piece 16 is connected to the apparatus main body 14. Accordingly, a situation where the abnormality judgment is made in the state where the hand piece 16 is not connected, and an abnormality notification frequently occurs is avoided.

Third Preferred Embodiment

The third preferred embodiment refers to an ultrasonic operation apparatus which detects an abnormality of a hand piece or a probe when the hand piece and the probe are connected to the ultrasonic operation apparatus after power-on. The third preferred embodiment of the present invention is described below.

FIG. 6 is a block diagram showing the ultrasonic operation apparatus according to the third preferred embodiment of the present invention. Constituent elements having functions similar to those in the second preferred embodiment are denoted with the same reference numerals, and their explanations are omitted. With reference to FIG. 6, the ultrasonic operation apparatus 12 according to this preferred embodiment makes abnormality judgment when the hand piece 16 is connected to the apparatus main body 14, and the probe 20 is connected to the hand piece 16.

In this preferred embodiment, the probe 20 is connectable/disconnectable to/from the hand piece 16. A controlling unit 24 has a function as probe connection detecting means for detecting whether or not the probe 20 is connected to the hand piece 16. Namely, the controlling unit 24 repeats judgment similar to the abnormality judgment after detecting that the hand piece 16 is connected, and judges that the probe 20 is connected if the judgment is initially made to be normal. Namely, in this preferred embodiment, a resonance frequency in a state where the probe 20 is connected to the hand piece 16 is detected. Even if an abnormality is judged, the abnormality is not notified until the probe 20 is judged to be connected, and it is merely judged that the probe 20 is not connected.

FIG. 7 is a flowchart for explaining a control performed by the ultrasonic operation apparatus according to the third preferred embodiment of the present invention. This figure depicts a flow for detecting an abnormality of the hand piece or the probe after the connections of the hand piece and the probe are verified subsequently to power-on.

Firstly, in step S10, the apparatus main body 14 is powered on. Then, in step S11, it is judged whether or not the hand piece 16 is connected, in a similar manner as in the second preferred embodiment. If it is judged in step S11 that the hand piece 16 is not connected, step S11 is repeated. Or, if it is judged in step S11 that the hand piece 16 is connected, the flow proceeds to step S12.

In step S12, it is judged whether or not the probe 20 is connected. Namely, the controlling unit 24 repeats judgment similar to the abnormality judgment after judging that the hand piece 16 is connected, and judges that the probe 20 is connected if the judgment is initially made to be normal. If it is judged in step S12 that the probe 20 is not connected, step S12 is repeated. Or, if it is judged in step S12 that the probe 20 is connected, the flow proceeds to step S20. Thereafter, the abnormality judgment is repeated in a similar manner as in the second preferred embodiment.

Accordingly, the ultrasonic operation apparatus 12 according to this preferred embodiment produces the following effect. If the abnormality judgment is made in a state where the probe 20 is not connected to the hand piece 16, the controlling unit 24 judges that the hand piece 16 or the probe 20 is abnormal. In this preferred embodiment, the abnormality judgment of the hand piece 16 or the probe 20 is made when the probe 20 is connected to the hand piece 16. Accordingly, a situation where the abnormality judgment is made in a state where the probe 20 is not connected, and an abnormality notification frequently occurs is avoided.

Fourth Preferred Embodiment

The fourth preferred embodiment refers to an ultrasonic operation apparatus which detects an abnormality of a hand piece or a probe subsequently to an output when the normal output is made from the hand piece after the hand piece is connected.

The fourth preferred embodiment of the present invention is described below. Constituent elements having functions similar to those in the third preferred embodiment are denoted with the same reference numerals, and their explanations are omitted. With reference to FIG. 6, the ultrasonic operation apparatus 12 according to this preferred embodiment makes abnormality judgment when the hand piece 16 is connected to an apparatus main body 14 and the probe 20 is connected to the hand piece 16, in a similar manner as in the third preferred embodiment. Note that, however, a method for detecting the connection between the hand piece 16 and the probe 20 is different from that in the third preferred embodiment.

In this preferred embodiment, the controlling unit 24 detects that the probe 20 is connected to the hand piece 16 when a normal output of the hand piece 16 is initially made with a first drive signal after detecting that the hand piece 16 is connected. Namely, if the controlling unit 24 judges that the hand piece 16 or the probe 20 is abnormal in the first output of the hand piece 16 after detecting that the hand piece 16 is connected, it judges that the probe 20 is not connected without issuing an abnormality notification. Or, if the controlling unit 24 judges that the hand piece 16 or the probe 20 are normal, it judges that the probe 20 is connected to the hand piece 16.

Figure 8:
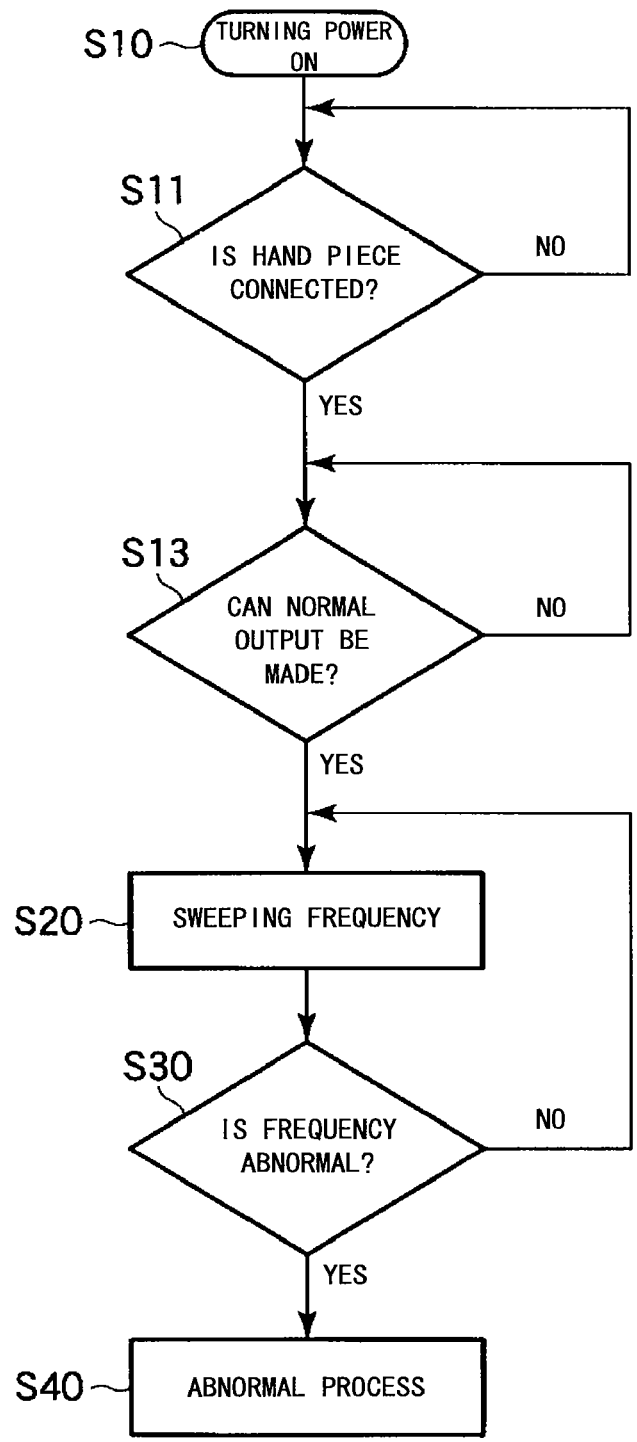
FIG. 8 is a flowchart for explaining a control performed by an ultrasonic operation apparatus according to a fourth preferred embodiment of the present invention.

FIG. 8 is a flowchart for explaining a control performed by the ultrasonic operation apparatus according to the fourth preferred embodiment of the present invention. This figure depicts a flow for repeating the abnormality detection of the hand piece or the probe after a normal output from the connected hand piece is verified subsequently to power-on.

Firstly, in step S10, the apparatus main body 14 is powered on. Then, in step S11, it is judged whether or not the hand piece 16 is connected, in a similar manner as in the third preferred embodiment. If it is judged in step S11 that the hand piece 16 is connected, the flow proceeds to step S13.

In step S13, it is judged whether or not the normal output of the hand piece 16 is made with the first drive signal. Namely, the controlling unit 24 stands by after judging that the hand piece 16 is connected. Then, the controlling unit 24 causes the hand piece 16 to make an output with the first drive signal if the first ON/OFF signal input from a foot switch receiving unit 26 is initially turned on, in a similar manner as in the first preferred embodiment. If it is judged that the hand piece 16 or the probe 20 is abnormal in this output, it is judged that the probe 20 is not connected to the hand piece 16. Or, if it is judged that the hand piece 16 and the probe 20 are normal, it is judged that the probe 20 is connected to the hand piece 16.

If it is judged in step S13 that the normal output of the hand piece 16 is not made with the first drive signal, namely, if it is judged that the probe 20 is not connected to the hand piece 16, step S13 is repeated. Or, if it is judged that the normal output of the hand piece 16 is made with the first drive signal, namely, if it is judged that the probe 20 is connected to the hand piece 16, the flow proceeds to step S20. Thereafter, the abnormality judgment is repeated in a similar manner as in the third preferred embodiment.

Accordingly, the ultrasonic operation apparatus 12 according to this preferred embodiment produces the following effect. If the probe 20 is connected to the hand piece 16 in a state where the second drive signal is output to the hand piece 16, the connection between the hand piece 16 and the probe 20 is difficult, and damage can sometimes occur when the connection is made. In this preferred embodiment, since the probe 20 is not connected to the hand piece 16 in the state where the second drive signal is output to the hand piece 16, a situation where damage can occur can be avoided.

Fifth Preferred Embodiment

The fifth preferred embodiment refers to an ultrasonic operation apparatus which detects an abnormality of a hand piece or a probe at predetermined time intervals by a predetermined number of times subsequently to an output when the normal output is made from the hand piece after the hand piece is connected. The fifth preferred embodiment of the present invention is described below.

Constituent elements having functions similar to those in the fourth preferred embodiment are denoted with the same reference numerals, and their explanations are omitted. With reference to FIG. 6, in the ultrasonic operation apparatus 12 according to this preferred embodiment, abnormality judgment is made when the hand piece 16 is connected to an apparatus main body 14 and the probe 20 is connected to the hand piece 16, in a similar manner as in the fourth preferred embodiment. Note that, however, the abnormality judgment with the second drive signal is made not repeatedly but at predetermined time intervals by a predetermined number of times.

Figure 9:
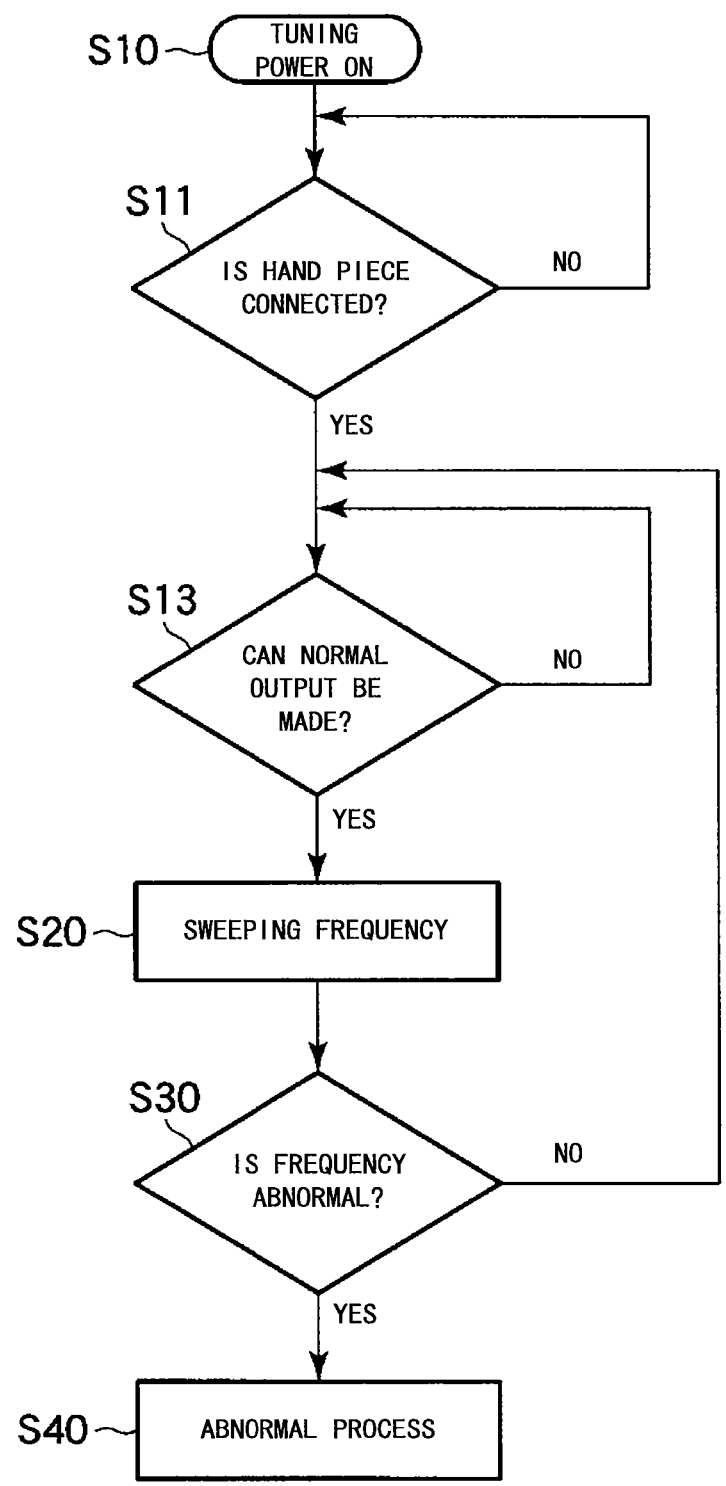
FIG. 9 is a flowchart for explaining a control performed by an ultrasonic operation apparatus according to a fifth preferred embodiment of the present invention.

FIG. 9 is a flowchart for explaining a control performed by the ultrasonic operation apparatus according to the fifth preferred embodiment of the present invention. This figure depicts a flow for detecting an abnormality of the hand piece or the probe at predetermined time intervals by a predetermined number of times after a normal output from the connected hand piece is verified subsequently to power-on. In a similar manner as in the fourth preferred embodiment, the apparatus main body 14 is powered on in step S10, it is judged in step S11 whether or not the hand piece 16 is connected, and it is judged in step S13 whether or not the normal output of the hand piece 16 is made, namely, whether or not the probe 20 is connected to the hand piece 16. Then, the abnormality judgment is made at predetermined time intervals by a predetermined number of times. In this preferred embodiment, the abnormality judgment is made only once (steps S20 and S30).

If it is judged that the hand piece 16 and the probe 20 are normal, the flow returns to step S13 and a standby is made until a foot switch 22 is again pressed. Namely, the abnormality judgment is not made until the output of the hand piece 16 is again made with the first drive signal, and accordingly, the probe 20 can be replaced during this time.

Accordingly, the ultrasonic operation apparatus 12 according to this preferred embodiment produces the following effect. If the probe 20 is disconnected from the hand piece 16 in a state where the second drive signal is output to the hand piece 16, the disconnection of the probe 20 from the hand piece is difficult and damage can sometimes occur when the probe 20 is disconnected. Since the second drive signal is not output to the hand piece 16 during an interval between outputs except for the instant following the output of the hand piece 16, the situation where damage can occur due to the disconnection made during this interval can be avoided.

Additionally, most of abnormalities of the hand piece 16 or the probe 20 occur during an output or immediately after an output. The abnormality judgment is made with the first drive signal along with an output during the output, and made with the second drive signal immediately after the output. Accordingly, the abnormality judgment is efficiently made, and unnecessary outputs of the drive signals are avoided.

Sixth Preferred Embodiment

The sixth preferred embodiment refers to an ultrasonic operation apparatus which detects an abnormality of a hand piece or a probe when an abnormality detection switch is pressed after the hand piece is connected. The sixth preferred embodiment of the present invention is described below.

Figure 10:
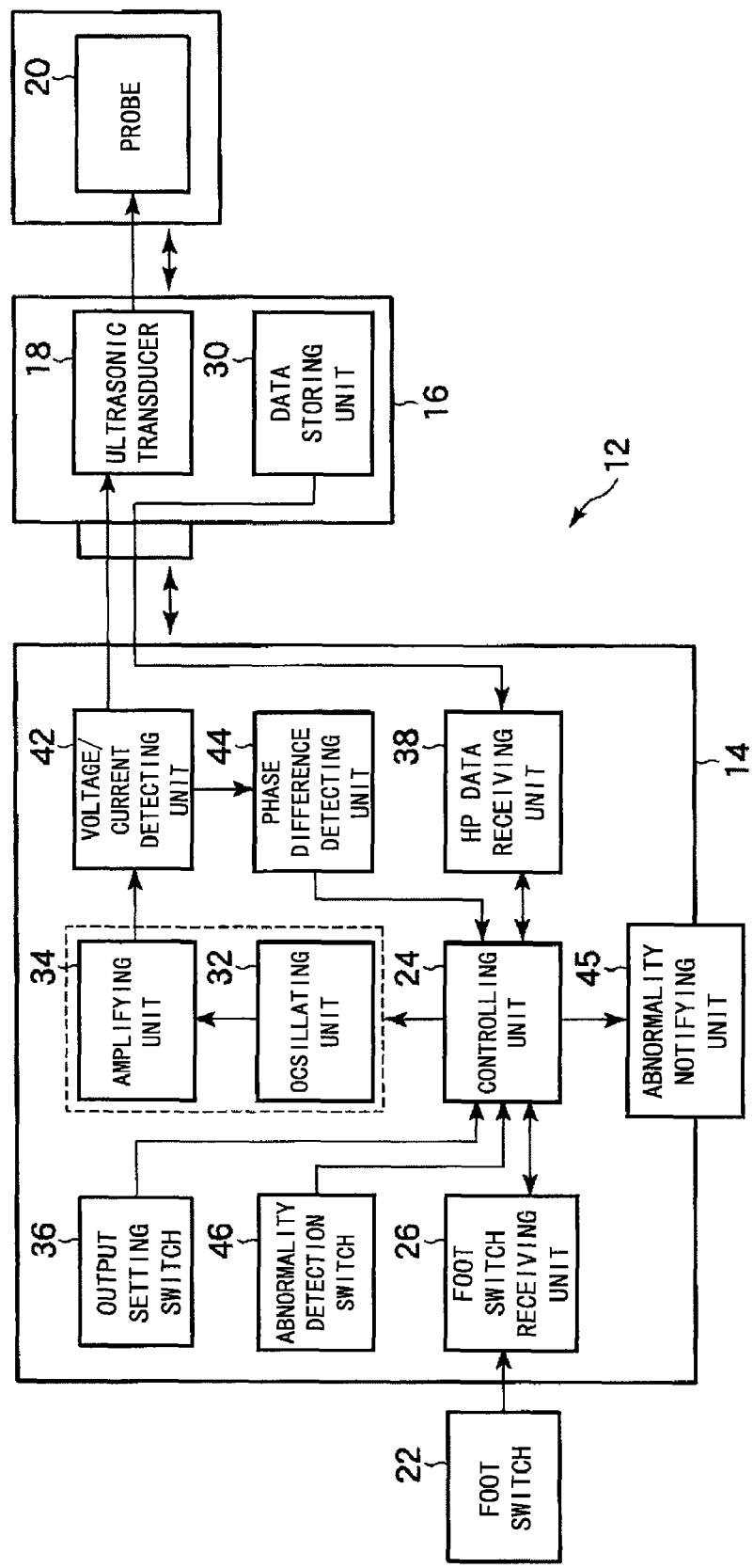
FIG. 10 is a block diagram showing an ultrasonic operation apparatus according to a sixth preferred embodiment of the present invention.

FIG. 10 is a block diagram showing the ultrasonic operation apparatus according to the sixth preferred embodiment of the present invention. Constituent elements having functions similar to those in the fifth preferred embodiment are denoted with the same reference numerals, and their explanations are omitted. With reference to FIG. 10, the ultrasonic operation apparatus 12 according to this preferred embodiment makes abnormality judgment when the abnormality detection switch 46 provided on an apparatus main body 14 is pressed.

Figure 11:
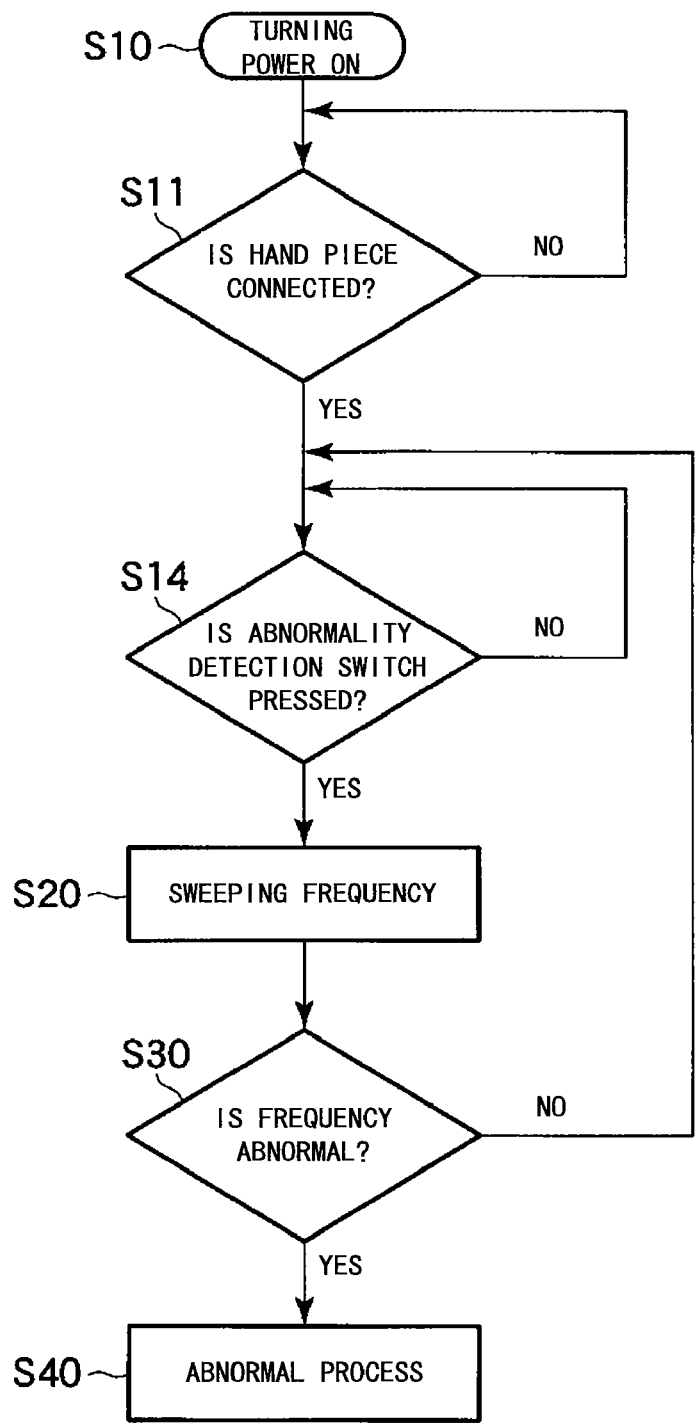
FIG. 11 is a flowchart for explaining a control performed by the ultrasonic operation apparatus according to the sixth preferred embodiment of the present invention.

FIG. 11 is a flowchart for explaining a control performed by the ultrasonic operation apparatus according to the sixth preferred embodiment of the present invention. This figure depicts a flow for detecting an abnormality of the hand piece or the probe when the abnormality detection switch is pressed after the hand piece is connected. In a similar manner as in the fifth preferred embodiment, the apparatus main body 14 is powered on in step S10, and it is judged in step S11 whether or not the hand piece 16 is connected. Thereafter, it is judged in step S14 whether or not the abnormality detection switch 46 is pressed. If it is judged in step S14 that the abnormality detection switch 46 is not pressed, step S14 is repeated. Or, if it is judged in step S14 that the abnormality detection switch 46 is pressed, the abnormality judgment is made at predetermined time intervals by a predetermined number of times. In this preferred embodiment, the abnormality judgment is made only once (steps S20 and S30). If it is judged that the hand piece 16 and the probe 20 are normal, the flow returns to step S14. Namely, the abnormality judgment is not made until the abnormality detection switch 46 is again pressed.

Accordingly, the ultrasonic operation apparatus 12 according to this preferred embodiment produces the following effect. The abnormality judgment can be made when the abnormality detection switch 46 is pressed, and the abnormality judgment can be made at a desired time, such as when an operator suspects an occurrence of an abnormality.

A modification example of the sixth preferred embodiment according to the present invention is described below. A controlling unit 24 of an ultrasonic operation apparatus 12 in this modification example has a function as setting state detecting means for detecting the setting state of the ultrasonic operation apparatus 12, and makes abnormality judgment if detecting that the setting is changed. The setting state of the ultrasonic operation apparatus 12 is changed with an output setting switch 36 for setting an output, a switch for changing the setting of a foot switch 22, or the like.

When an abnormality is notified in this preferred embodiment, the first and the second drive signals are stopped. In this case, an operator can restore the ultrasonic operation apparatus 12 to a normal state, for example, by replacing the hand piece 16 or the probe 20. Alternatively, it may also be configured that the second drive signal is not stopped even when an abnormality is notified, and the ultrasonic operation apparatus 12 is restored to a normal state, for example, by replacing the hand piece 16 or the probe 20 in a state where the second drive signal is output.

According to the present invention, an abnormality of an ultrasonic operation apparatus can be detected even when an output is not made, and a configuration of the ultrasonic operation apparatus is simple.

What is claimed is:

1. An ultrasonic operation apparatus, comprising:
a hand piece accommodating an ultrasonic transducer for generating ultrasonic vibrations;
a probe which is removably connected to said hand piece and to which the ultrasonic vibrations are conveyed, the probe being connectable to and disconnectable from the hand piece;
a drive signal generating unit for generating a first drive signal that drives the ultrasonic transducer, and a second drive signal, an output level of the second drive signal being different from an output level of the first drive signal, and the drive signal generating unit being operable for outputting the first and second drive signals to the ultrasonic transducer;
an output detecting unit for detecting an output current and an output voltage of the second drive signal to the ultrasonic transducer; and
a controlling unit which controls operations of said drive signal generating unit based on a phase difference between the output voltage and the output current of the second drive signal for making a judgment on a running state of said probe or said hand piece by determining whether or not a second resonance frequency can be detected within a predetermined range, the second resonance frequency being a frequency at which the phase difference between the output voltage and the output current of the second drive signal becomes almost zero, wherein the controlling unit detects whether the probe and the hand piece are connected and makes the judgment when detecting that the probe and the hand piece are connected.

2. The ultrasonic operation apparatus according to claim 1, wherein
said controlling unit judges that said probe or said hand piece is abnormal if the resonance frequency at which the phase difference between the output voltage and the output current of the second drive signal becomes almost zero cannot be detected within the predetermined range.

3. The ultrasonic operation apparatus according to claim 1, further comprising
a power detecting unit for detecting ON/OFF of power of the ultrasonic operation apparatus, wherein said controlling unit makes the judgment if said power detecting unit detects that the power is turned on.

4. The ultrasonic operation apparatus according to claim 1, wherein
said hand piece is connectable/disconnectable to/from the ultrasonic operation apparatus; and said controlling unit makes the judgment when detecting that said hand piece is connected to the ultrasonic operation apparatus.

5. The ultrasonic operation apparatus according to claim 4, wherein
said controlling unit detects that said hand piece is connected to the ultrasonic operation apparatus if said controlling unit can obtain predetermined data stored in a storing unit, which is provided in said hand piece.

6. The ultrasonic operation apparatus according to claim 1, wherein said controlling unit determines that said probe and said hand piece are connected if the controlling unit detects the second resonance frequency as being within the predetermined range when the output level of the second drive signal is changed.

7. The ultrasonic operation apparatus according to claim 1, wherein
said output detecting unit further detects an output current and an output voltage of the first drive signal to said hand piece; and
said controlling unit detects that said probe and said hand piece are connected if a first resonance frequency can be detected within a predetermined range when the output level of the first drive signal is changed, the first resonance frequency being a frequency at which a phase difference between the output voltage and the output current of the first drive signal becomes almost zero.

8. The ultrasonic operation apparatus according to claim 1, wherein said controlling unit makes the judgment by a predetermined number of times.

9. The ultrasonic operation apparatus according to claim 1, further comprising
an abnormality detection switch, wherein said controlling unit makes the judgment when said abnormality detection switch is turned on.

10. The ultrasonic operation apparatus according to claim 1, further comprising a setting state detecting unit for detecting a setting state of the ultrasonic operation apparatus, wherein said controlling unit makes the judgment when said setting state detecting unit detects that the setting state is changed.

11. The ultrasonic operation apparatus according to claim 1, wherein
data about at least a frequency range where a drive frequency of the first drive signal or the second drive signal is swept, and a predetermined frequency range within the frequency range are stored in a storing unit provided in said hand piece; and said controlling unit obtains the data, and controls said drive signal generating unit based on the obtained data so that the drive frequency of the first drive signal or the second drive signal is swept.

12. An abnormality judgment method of an ultrasonic operation apparatus, which comprises a hand piece accommodating an ultrasonic transducer for generating ultrasonic vibrations, and a probe which is removably connectable to and disconnectable from the hand piece and to which the ultrasonic vibrations are conveyed, the method comprising:

generating a first drive signal that drives the ultrasonic transducer, generating a second drive signal, an output level of said second drive signal being different from an output level of the first drive signal, and outputting the first and the second drive signals to the ultrasonic transducer;

detecting an output current and an output voltage of the second drive signal to the ultrasonic transducer;

detecting whether the probe is connected to the hand piece; and making a judgment on a running state of the probe or the hand piece by determining whether or not a second resonance frequency can be detected within a predetermined range, the second resonance frequency being a frequency at which a phase difference between the output voltage and the output current becomes almost zero, wherein the judgment is made when the probe is detected to be connected to the hand piece.

13. The abnormality judgment method according to claim 12, further comprising judging that the probe or the hand piece is abnormal if the second resonance frequency cannot be detected within the predetermined range, when making the judgment on the running state of the probe or the hand piece.

14. The abnormality judgment method according to claim 12, further comprising:

detecting ON/OFF of power of the ultrasonic operation apparatus; and making the judgment when detecting that the power is turned on.

15. The abnormality judgment method according to claim 12, further comprising:

detecting whether or not the hand piece, which is connectable/disconnectable to/from the ultrasonic operation apparatus, is connected to the ultrasonic operation apparatus; and making the judgment when detecting that the hand piece is connected to the ultrasonic operation apparatus.

16. The abnormality judgment method according to claim 15, further comprising detecting that the hand piece is connected to the ultrasonic operation apparatus if predetermined data stored in a storing unit, which is provided in the hand piece, can be obtained.

17. The abnormality judgment method according to claim 12, further comprising:

changing the output level of the second drive signal;

detecting the second resonance frequency after said changing of the output level of the second drive signal; and determining that the probe and the hand piece are connected when the second resonance frequency is detected to be within the predetermined range.

18. The abnormality judgment method according to claim 12, further comprising:

detecting an output current and an output voltage of the first drive signal to the hand piece;

changing the output level of the first drive signal;

detecting a first resonance frequency at which a phase difference between the output voltage and the output current of the first drive signal becomes almost zero; and determining that the probe and the hand piece are connected when the first resonance frequency is detected to be within the predetermined range.

19. The abnormality judgment method according to claim 12, further comprising making the judgment by a predetermined number of times.

20. The abnormality judgment method according to claim 12, wherein:

the ultrasonic operation apparatus further comprises an abnormality detection switch; and the judgment is made when the abnormality detection switch is turned on.

21. The abnormality judgment method according to claim 12, further comprising:

detecting a setting state of the ultrasonic operation apparatus; and making the judgment when detecting that the setting state of the ultrasonic operation apparatus is changed.

22. The abnormality judgment method according to claim 12, further comprising:

obtaining data of at least a frequency range where a drive frequency of the first drive signal or the second drive signal is swept, and a predetermined frequency range within the frequency range from a storing unit provided in the hand piece; and sweeping the drive frequency of the first drive signal or the second drive signal based on the obtained data.

* * * * *